US012766215B2

United States Patent

(12) United States Patent
Wang et al.

(10) Patent No.: US 12,766,215 B2
(45) Date of Patent: Oct. 20, 2026

(54) STERILIZATION AND DEODORIZATION WASTE CONTAINER

(71) Applicant: Shi Ping Wang, Fuzhou (CN)

(72) Inventors: Shi Ping Wang, Fuzhou (CN); Jiangqun Chen, Fuzhou (CN); Youxi Lou, Fuzhou (CN); Zhou Lin, Fuzhou (CN)

(73) Assignees: Nhe Stars Group (U.S.A.) Inc., Ontario, CA (US); Fujian Nashida Bectronic Incorporated Company, Fuzhou (CN)

( * ) Notice: Subject to any disclaimer, the term of this patent is extended or adjusted under 35 U.S.C. 154(b) by 499 days.

(21) Appl. No.: 18/222,383

(22) Filed: Jul. 14, 2023

(65) Prior Publication Data

US 2023/0355828 A1 Nov. 9, 2023

Related U.S. Application Data

(63) Continuation-in-part of application No. 18/266,587, filed as application No. PCT/CN2021/109449 on Jul. 30, 2021.

(30) Foreign Application Priority Data

Jul. 30, 2021 (WO) ................ PCT/CN2021/109449

(51) Int. Cl.
*A61L 11/00* (2006.01)
*B65F 1/14* (2006.01)

(52) U.S. Cl.
CPC ................. *A61L 11/00* (2013.01); *B65F 1/14* (2013.01)

(58) Field of Classification Search
CPC ................ A61L 11/00; A61L 2209/111; A61L 2209/12; A61L 2209/212; A61L 9/015;
(Continued)

(56) References Cited

U.S. PATENT DOCUMENTS 5,337,581 A * 8/1994 Lott ........................ A61L 11/00 422/292
2007/0295355 A1* 12/2007 Ikuta ................ H01L 21/67115 134/1
(Continued)

FOREIGN PATENT DOCUMENTS

CN 110733785 A * 1/2020 ................ B65F 1/14

*Primary Examiner* — Jennifer Wecker
*Assistant Examiner* — Brady C Pilsbury
(74) *Attorney, Agent, or Firm* — David & Raymond Patent Farm; Raymond Y. Chan

(57) ABSTRACT

A sterilization and deodorization waste container includes an isolation chamber provided on an inner side of a container lid and a dual-wave band ultraviolet lamp tube installed in the isolation chamber. The dual-wave band ultraviolet lamp tube is capable of simultaneously generating a direct ultraviolet light wave and an ozone ultraviolet light wave. The isolation chamber includes a reflector housing having a light transmitting window facing an inner cavity of a container body. The dual-wave band ultraviolet lamp tube is controlled by a control circuit to turn on to generate the ultraviolets into an inner cavity of the container body while the container lid is closed and to turn off to stop generating the ultraviolet while the container lid is opened.

5 Claims, 7 Drawing Sheets

(58) Field of Classification Search
CPC .... A61L 9/20; A61L 2202/11; A61L 2202/14; A61L 2/10; B65F 1/14; B65F 1/06; B65F 1/163; B65F 2210/168; B65F 7/00
See application file for complete search history.

(56) References Cited

U.S. PATENT DOCUMENTS

2020/0390917 A1* 12/2020 Tang .......................... A61L 2/10
2020/0391940 A1* 12/2020 Wang ........................ B65F 1/02

* cited by examiner

STERILIZATION AND DEODORIZATION WASTE CONTAINER

CROSS REFERENCE OF RELATED APPLICATION

This application is a Continuation-In-Part application that claims the benefit of priority under 35 U.S.C. § 120 to a non-provisional application, application Ser. No. 18/266,587, filed Jun. 9, 2022, which is a non-provisional application U.S. National Stage under 35 U.S.C. 371 of the International Application Number PCT/CN2021/109449, filed Jul. 30, 2021, which claims priority to Chinese application number 202022965269,7, filed Dec. 12, 2020, which are incorporated herewith by references in their entireties.

BACKGROUND OF THE PRESENT INVENTION

Field of Invention

The present invention relates to a sterilization and deodorization waste container, in particular a sterilization and deodorization waste container with dual-wave band ultraviolet lamp tube. The invention is adapted for waste containers with lids.

Description of Related Arts

Current household waste containers are generally equipped with lids configured to be opened by means of foot pedal, induction, gentle touch, and etc. In particular, in the waste container used in the kitchen, the kitchen waste disposed in the barrel is easy to breed bacteria and generate stinky smell, resulting in pollution of people's living environment. That further affects people's sense of smell and health and has health hazards. In order to solve the above problems, the current technology utilizes ultraviolet light wave for sterilization. That is, a direct ultraviolet lamp tube is installed in the waste container to sterilize the interior environment in the barrel, but this solution of using ultraviolet for direct sterilization has the following shortcomings:

1. The ultraviolet directly irradiated by ultraviolet lamp tube for sterilization can only propagate along a straight line, and thus there are more positions that cannot be irradiated and dead angles during the sterilization in the container. Therefore, its sterilization effect is relatively poor.
2. In order to ensure light transmission and sterilization effect, the ultraviolet lamp tube in the current technology often adopts a naked installation method. That is, the ultraviolet lamp tube is arranged to face the interior of the container without obstruction. Due to the harsh environment within the container, the operating condition of the ultraviolet lamp tube is adversely affected directly, so that its service life span is also greatly shortened, the cost of use is high, and it is difficult to promote.

SUMMARY OF THE PRESENT INVENTION

In view of the shortcomings of the current technology, an objective of the invention is to provide a sterilization and deodorization waste container having dual-wave band ultraviolet lamp tube that avoids sterilization dead angle, enhances the sterilization effect, improves the operating environment of the ultraviolet lamp, improves service life span thereof, and reduces the cost of use.

Another objective of the invention is to provide a sterilization and deodorization waste container which automatically processes sterilization and deodorization while its container lid is in close state and stops sterilization and deodorization while its container lid is in open state or the container lid is detached from the container body.

Another objective of the invention is to provide a sterilization and deodorization waste container equipped with a dual-wave band ultraviolet sterilization and deodorization arrangement which is adapted to be installed in the container lid and configured for propagating ultraviolets in the inner cavity of the container body for sterilization and deodorization of the waste contained in the inner cavity.

Another objective of the invention is to provide a dual-wave band ultraviolet sterilization and deodorization arrangement which is appliable to all types of waste container, including foot pedal waste container, induction waste container, touch waste container, and etc.

Another objective of the invention is to provide a dual-wave band ultraviolet sterilization and deodorization arrangement for waste container, which is automatically operated to start generating ultraviolets and stop generating ultraviolets according to the closing and opening of the container lid with respect to the container body.

Another objective of the invention is to provide a dual-wave band ultraviolet sterilization and deodorization arrangement for waste container having an inner cavity for storing waste, which comprises an ultraviolet generator and a control means, wherein the ultraviolet generator comprises a dual-wave band ultraviolet lamp tube arranged in the waste container and configured to generate ultraviolets with a direct sterilization ultraviolet light wave propagating directly to the waste container the inner cavity of the waste container for direct sterilization and an ozone sterilization ultraviolet light wave dispersing and diffusing in the inner cavity of the waste container for ozone sterilization, wherein the control means is arranged for turning off dual-wave band ultraviolet lamp tube while the inner cavity of the waste container is accessible to outside and turning on the dual-wave band ultraviolet map tube while the inner cavity waste container is in closed from outside.

Additional advantages and features of the invention will become apparent from the description which follows and may be realized by means of the instrumentalities and combinations particular point out in the appended claims.

According to the invention, the foregoing objective is attained by:

a sterilization and deodorization waste container having dual-wave band ultraviolet lamp tube, which includes a container body, a container lid and a control circuit, wherein one or more structural characteristic in further including an isolation chamber installed on an inner side of the container lid and a dual-wave band ultraviolet lamp tube arranged in the isolation chamber, the dual-wave band ultraviolet lamp tube being a lamp tube capable of simultaneously generating a direct sterilization ultraviolet light wave and ozone sterilization ultraviolet light wave, the isolation chamber comprising a reflector housing and a transparent quartz glass, an opening of the reflector housing facing an inner cavity of the container body, shape and size of the transparent quartz glass fitting and matching to an opening surface of the reflector housing and being covered and connected to the opening of the reflector housing through a sealing silicone ring cover; a control input terminal of a driving circuit of the dual-wave band ultraviolet lamp tube being connected to a driving control terminal of the control circuit by a control switch.

In accordance with another aspect of the invention, the present invention comprises a dual-wave band ultraviolet sterilization and deodorization arrangement for a waste container including a container body having a container opening and an inner cavity for storing waste and a container lid configured to be mounted on top of the container opening to cover the inner cavity of the container body, wherein the dual-wave band ultraviolet sterilization and deodorization arrangement comprises:

an isolation chamber comprising a reflector housing, configured for installing below the container lid of the waste container, having a light-transmitting window formed in a lower side thereof;

a dual-wave band ultraviolet lamp tube arranged in the reflector housing and configured to generate ultraviolets, including a direct sterilization ultraviolet light wave having a wave length between 253.7 nm to 254 nm and an ozone sterilization ultraviolet light wave having a wave length between 165 nm to 200 nm, such that the ultraviolets are arranged to propagate out through the light-transmitting window; and a control circuit configured to selectively turn on the dual-wave band ultraviolet lamp tube to propagate the ultraviolets and turn off the dual-wave band ultraviolet lamp tube to stop propagating the ultraviolets.

In one embodiment, the reflector housing has an opening in the lower side and the light-transmitting window is a transparent quartz glass fittingly and sealingly mounted at the opening of the reflector housing for facing the inner cavity of the container body.

In one embodiment, a reflective surface is provided at an upper side of the reflector housing, wherein a lower side of the dual-wave band ultraviolet lamp tube sealingly arranged in the isolation chamber faces the light-transmitting window of the isolation chamber and an upper side of the dual side of the dual-wave band ultraviolet lamp tube faces the reflective surface of the isolation chamber such that a portion of the ultraviolets propagating upward is reflected by the reflecting surface to propagate downwards through the light-transmitting window into the inner cavity of the container body.

In one embodiment, the control circuit is configured to selectively control the dual-wave band ultraviolet lamp tube to turn off to stop generating the ultraviolets while the container lid is opened with respect to the container body and to turn on to generate the ultraviolets while the container lid is closed with respect to the container body.

In one embodiment, the control circuit comprises at least one detecting control element and at least one control driving element which are installed on the container body and the container lid respectively in such a manner that when the container lid is opened, the control driving element leaves a detection range of the detecting control element, the control circuit controls the dual-wave band ultraviolet lamp tube to turn off to stop generating the ultraviolets, and that when the container lid is closed in place, the detecting control element detects an approaching of the control driving element and the control circuit controls the dual-wave band ultraviolet lamp tube to turn on to generate the ultraviolets.

In one embodiment, the detecting control element is selected from a group consisting of Hall element, position limiting switch and an angle sensor.

In one embodiment, the detecting control element is a Hall element and the control driving element is a magnet.

In one embodiment, the control driving element is provided under the container lid and the detecting control element is provided in the waste container where the detecting control element is able to detect a distance between the detecting control element and the control driving element to determine whether the contain lid is in a close state or open state with respect to the container body.

In one embodiment, the container lid comprises a ring shape shell arranged to be mounted on top of the container body and a cover panel pivotally connected to the ring shape shell for closing a lid opening of the ring shape shell and the container opening of the container body, wherein the control circuit comprises two pairs of detecting control element and control driving element, wherein the two detecting control elements are installed on the ring shape shell and the two control driving elements are installed on the container body and the cover panel respectively, such that when one of the detecting control elements leaves the corresponding control driving element while either the cover panel or the ring shape shell is opened with respect to the container body, the control circuit controls the dual-wave band ultraviolet lamp tube to turn off to stop generating the ultraviolets, and that when both the ring shape shell and the cover panel are closed in place with respect to the container body, the detecting control elements detect an approaching of the corresponding control driving element and the control circuit controls the dual-wave band ultraviolet lamp tube to turn on to generate the ultraviolets.

In accordance with another aspect of the invention, the present invention provides a sterilization and deodorization method of a waste container, comprising steps of:

(a) turning on a dual-wave band ultraviolet lamp tube, sealed in an isolation chamber provided below a container lid of the waste container, to generate ultraviolets, including a direct sterilization ultraviolet light wave having a wavelength between 240 nm to 280 nm and an ozone sterilization ultraviolet light wave having a wavelength between 165 nm to 200 nm, propagating through a light-transmitting window of the isolation chamber into an inner cavity of the waste container, while the container lid is in a close state with respect to the container body; and (b) turning off the dual-wave band ultraviolet lamp tube to stop generating the ultraviolets while the inner cavity of the container body is accessible to outside.

In one embodiment, in the step (b), the inner cavity of the container body is accessible to outside when the container lid is opened with respect to the container body.

In one embodiment, in the step (b), the inner cavity of the container is accessible to outside when the ring shape shell is separated from the container body.

Accordingly, the invention includes the following distinctive features:

1) By means of the isolation chamber provided to isolate with outside air, the dual-wave band ultraviolet lamp tube is sealingly contained between the reflector housing and the sealedly connected transparent quartz glass. Therefore, the glass surface may merely be wiped while it is dirty and the harsh environment in the waste container is prevented to affect the ultraviolet lamp tube in the isolation chamber, that optimizes the operating environment of the ultraviolet lamp tube, improves the service life span thereof and reduces the cost of use.

2) The transparent quartz glass is capable of enhancing a light transmittance of the ultraviolet light. The reflector housing can reflect most of the other ultraviolet light waves in the isolation chamber to penetrate through the transparent quartz glass into the container body, that greatly increases the intensity and number of effective light waves, and solves the conventional problems of light transmission and irradiation of the ultraviolet lamp tube.

3) The dual-wave band ultraviolet lamp tube provides double sterilizations, direct sterilization and ozone sterilization, wherein the ultraviolet light wave for direct sterilization has high photon energy to penetrate the cell membrane and nucleus of microorganisms, destroy the molecular bonds of their DNA, and kill them by making them lose replication ability or activity, and the ultraviolet light wave for ozone sterilization can turn O2 (oxygen) in the air into O3 (ozone) which has a strong oxidation effect that can diffuse in the container body and effectively kill bacteria. Ozone dispersion characteristics can just make up for the shortcomings of the ultraviolet for direct sterilization, including it only propagates along the straight line and the disinfection has dead angles. The two types of sterilization ultraviolet wave can sufficiently and effectively disinfect and sterilize the interior of the waste container, greatly improving the sterilization effect. In addition, during the disinfection and oxidation process, excess ozone will combine to become oxygen within 30 min to avoid ozone pollution.

4) The arrangement of the isolation chamber provides an excel environment for ozone sterilization of the ultraviolet light wave for ozone sterilization: Since ozone is highly corrosive, under the arrangement of the isolation chamber, ozone can only be diffused in the isolation chamber and the inner cavity of the container body, without affecting the electric circuit components and mechanical components within the interior space of the container lid.

In particular, the invention can further be embodied as follows:

The reflector housing is either a plastic electroplated member, or a resin shell body with a reflective film formed on inner side surfaces thereof, or a stainless steel made metal member with reflective arrangement on inner side surfaces thereof.

The reflector housing is preferred to be made of materials that are not easy to age, not easy to be corroded and oxidized, to avoid ozone corrosion and improve the reflection effect of light waves.

The ultraviolet light wave for direct sterilization is 240-280 nm ultraviolet light wave, preferably an ultraviolet light wave with a wavelength of 254 nm for direct sterilization.

The ultraviolet light wave for direct sterilization is also known as short-wave sterilization ultraviolet (UVC). The 253.7-254 nm wavelength ultraviolet light has the strongest photon energy and the best sterilization effect.

The ultraviolet light wave for ozone sterilization is 165-200 nm ultraviolet light wave, preferably an ultraviolet light wave with a wavelength of 185 nm for ozone sterilization.

The ultraviolet light wave (part of the UVD light wave) for ozone sterilization irradiated in the air can turn O2 (oxygen) in the air into O3 (ozone), wherein the 185 nm ozone sterilization ultraviolet light wave is the band with better effect.

The sealing silicone ring is a sealing ring having a cross-sectional inverted U-shape, such that a peripheral edge portion of the transparent quartz glass is positioned in an inner cavity of the U-shaped sealing ring, whereby the peripheral edge portion of the transparent quartz glass is completely covered in the sealing silicone ring.

The configuration of completely covering the peripheral edge of the transparent quartz glass can reduce damage caused by vibrations of the transparent quartz glass due to the vibration of the isolation chamber installed below the container lid while being flipped up and down frequently, so as to ensure the reliability of the structure. In addition, silicone can also prevent aging caused by ultraviolet radiation.

The control switch, which is either a Hall sensor, or an angle sensor, or a position limiting switch, comprises a control driving element and a detecting control element arranged in a separable manner, the control driving element being connected to the dual-wave band ultraviolet lamp tube and the control circuit.

For example, the control driving element of the angle sensor can be installed on a main rotating shaft of the container lid. When the container lid (or cover panel while the container lid is composed of a cover panel and a ring shape shell) opens at a certain angle (that is, when the container lid or cover panel is flipped up to open), the control circuit cuts off a power supply to the ultraviolet lamp tube while receiving a signal of the angle sensor and turns it off. When the container lid (or cover panel) is flipped down to close to a predetermined angle (when the container lid or cover panel is fully closed), the ultraviolet lamp tube is controlled to turn on for sterilization. For example, while the Hall sensor includes a Hall element as the control driving element and a magnet as the detecting control element, the ultraviolet lamp tube is turned off when the magnet leaves the detection range of the Hall element (i.e. when the container lid or cover panel is flipped up to open), and the ultraviolet lamp tube is turned on when the magnet enters the detection range of the Hall element (when the container lid or cover panel is flipped down to close). Accordingly, when the container lid or cover panel is opened, the control switch sends a signal and the control circuit controls the dual-wave band ultraviolet lamp tube to turn off to avoid ultraviolet from hurting human skin and eyes, and when the container lid or cover is closed, the control switch sends a signal to make the control circuit to timely turn on the ultraviolet lamp tube to sterilize the interior of the contain body in time.

One side of the container lid is pivotally connected with the container body, and a case is arranged at a hinging side of the container lid for receiving the control circuit. The case has a cavity provided therein and the insolation chamber is provided in the cavity. The control driving element and the detecting control element of the control switch are installed on the container lid and the container body respectively.

When the container lid and the container body are embodied as an inseparable connection structure, the isolation chamber is being flipped up and down with the container lid, so that the control switch is preferred to be installed on a side of the container lid or an open edge thereof.

The container lid comprises a ring shape shell and a cover panel. A side edge of the cover panel is hinged with the ring shape shell. The ring shape shell is sleeved to the container body, wherein a control circuit is installed in an inner cavity of the ring shall shell and the isolation chamber is arranged in a cavity provided in the ring shape shell; The control switch includes two sets, the control driving element and the detecting control element of one of the two sets are installed on the ring shape shell and the container body respectively, and the control driving element and the detecting control element of another set are installed on the cover panel and the ring shape shell respectively.

In normal use, the control switch can be triggered by flipping the cover panel up or down. When it is necessary to detach the ring shape shell from the container body, the control switch can also be triggered, so as to effectively avoid harmful to the human body caused by ultraviolet leakage.

In view of above, the invention provides a sterilization and deodorization waste container with dual-wave band ultraviolet lamp tube, which utilizes an isolation chamber with the reflector housing and the transparent quartz glass to install the dual-wave band ultraviolet lamp tube, that effectively improves the operating environment of the ultraviolet lamp tube while avoiding influence on the internal circuit and mechanical components outside the isolation chamber, improves the service life span and reduces the cost of use. The drawbacks of light transmission and irradiation of ultraviolet lamp tube are resolved. The double ultraviolet sterilizations can substantially and effectively disinfect and sterilize the waste container that greatly improves the sterilization effect.

Still further objects and advantages will become apparent from a consideration of the ensuing description and drawings.

These and other objectives, features, and advantages of the present invention will become apparent from the following detailed description, the accompanying drawings, and the appended claims.

DESCRIPTION OF THE REFERENCE NUMBERS IN THE DRAWING

1—Container Lid, 10—Lid Opening, 11—Ring Shape Shell, 111—Ring Shape Barrel Head, 112—Ring Shape Retainer Body, 12—Cover Panel, 13—Control Circuit, 131—Detecting Control Element (Hall Element), 132—Control Driving Element (Magnet), 133—Detecting Control Element (Hall Element), 134—Control Driving Element (Magnet), 14—Lid Opening and Closing Driving Device, 2—Container Body, 20—Container Opening, 3—Isolation chamber, 30—Opening, 31—Reflector Housing, 311—Reflective Surface, 32—Transparent Quartz Glass, 321—Sealing Silicone Ring, 33—Dual-Wave Band Ultraviolet Lamp Tube, 331—Lamp Tube Body, 332—lamp Tube Body, 34—Ultraviolet Lamp Tube Driver Circuit, 4—Hinge Mechanism.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 4:
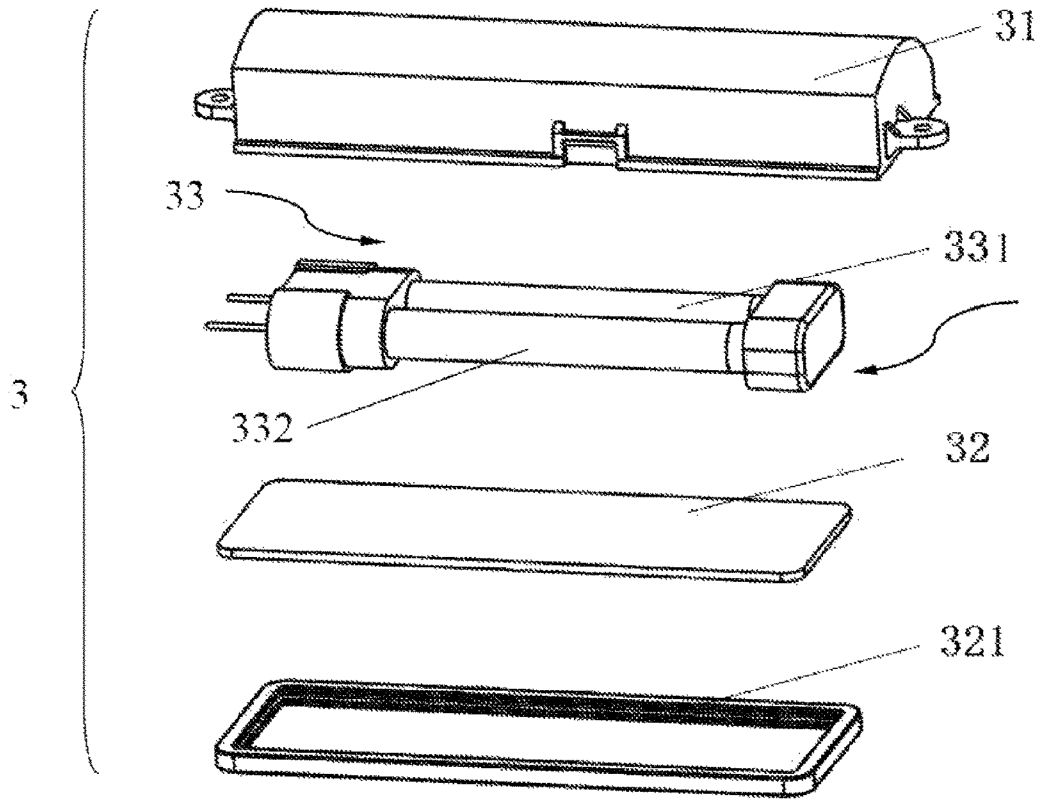
FIG. 4 is an exploded structural perspective view of the isolation chamber.
Figure 5:
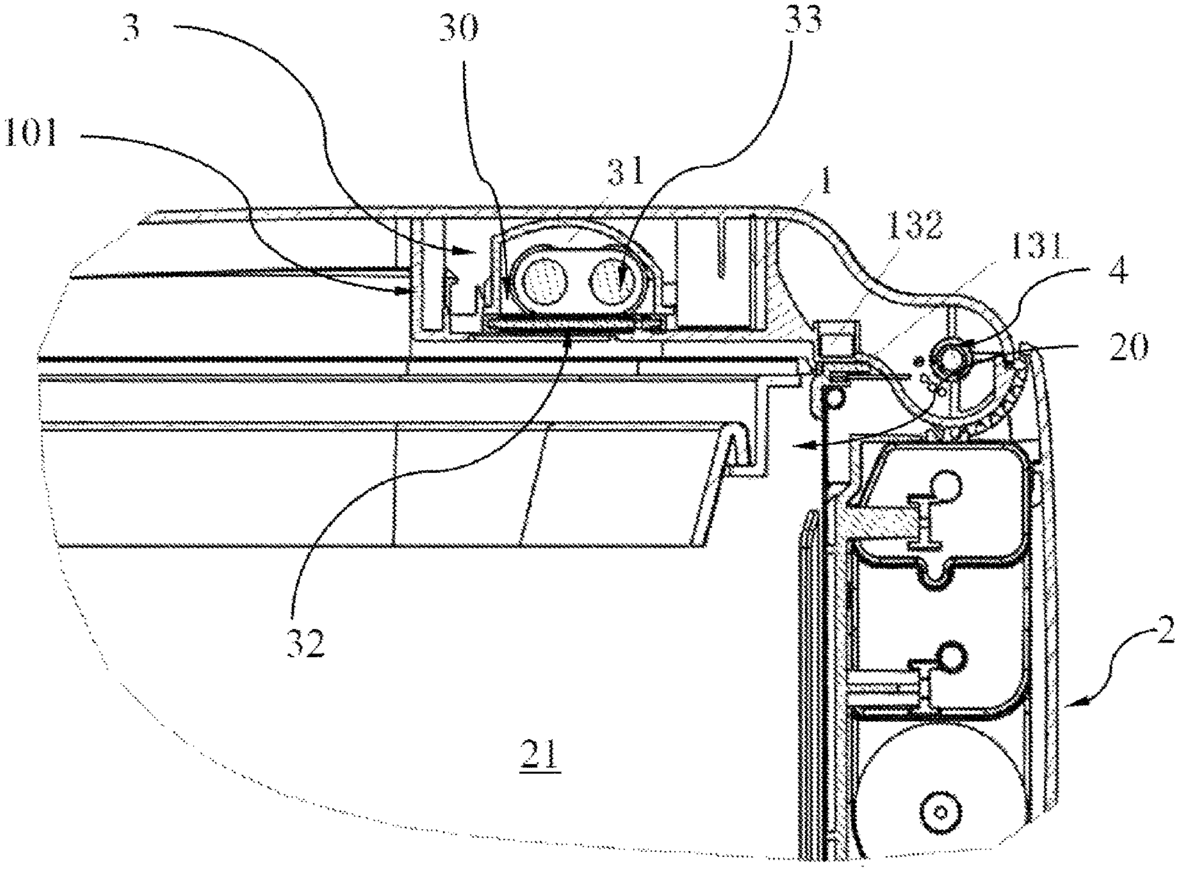
FIG. 5 is a partial structural sectional view of the sterilization and deodorization waste container with the dual-wave band ultraviolet lamp tube as shown in FIG. 1 according to the first embodiment of the invention.
Figure 6:
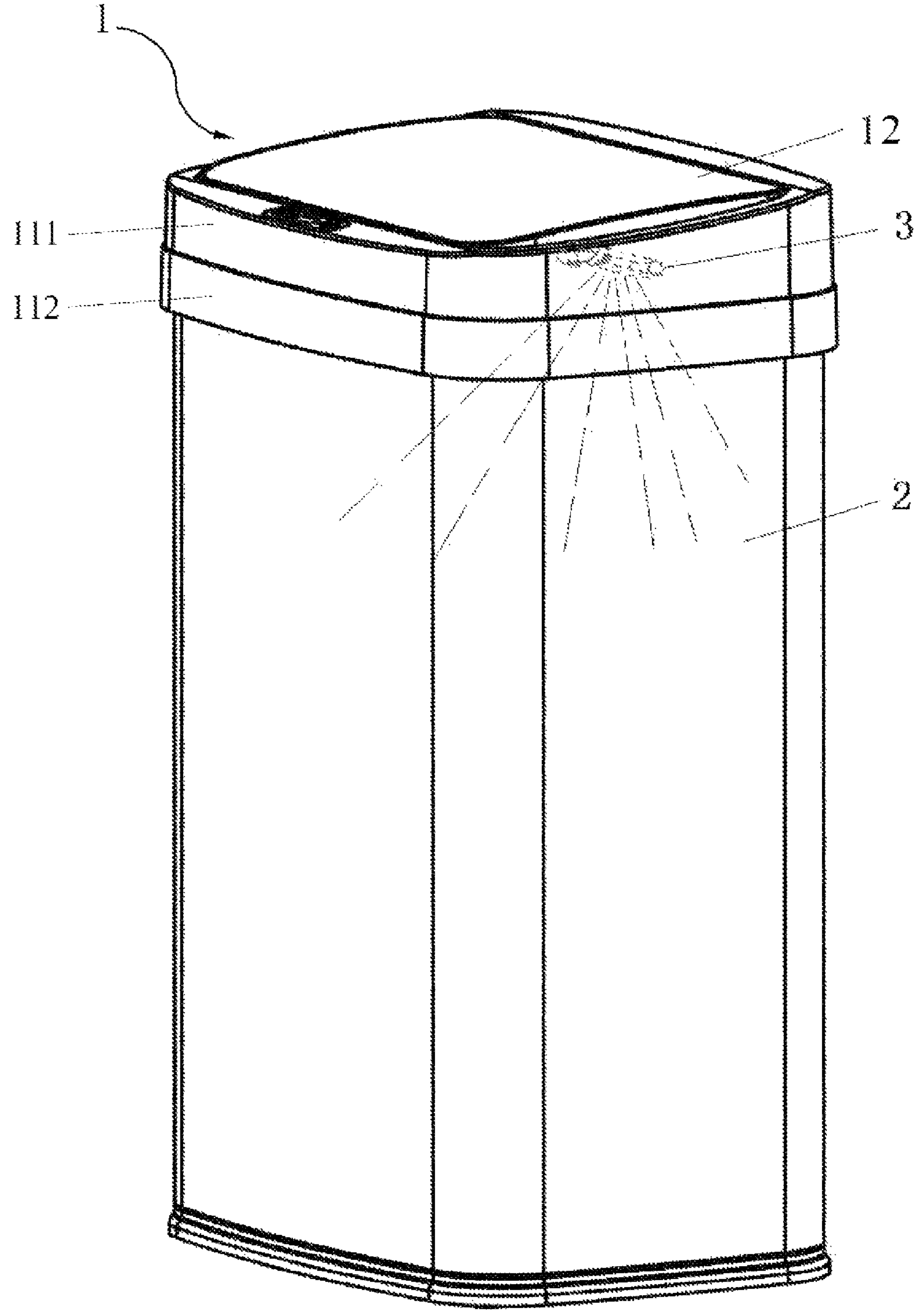
FIG. 6 is a perspective view of the sterilization and deodorization waste container with the dual-wave band ultraviolet lamp tube according to a second embodiment of the invention.
Figure 7:
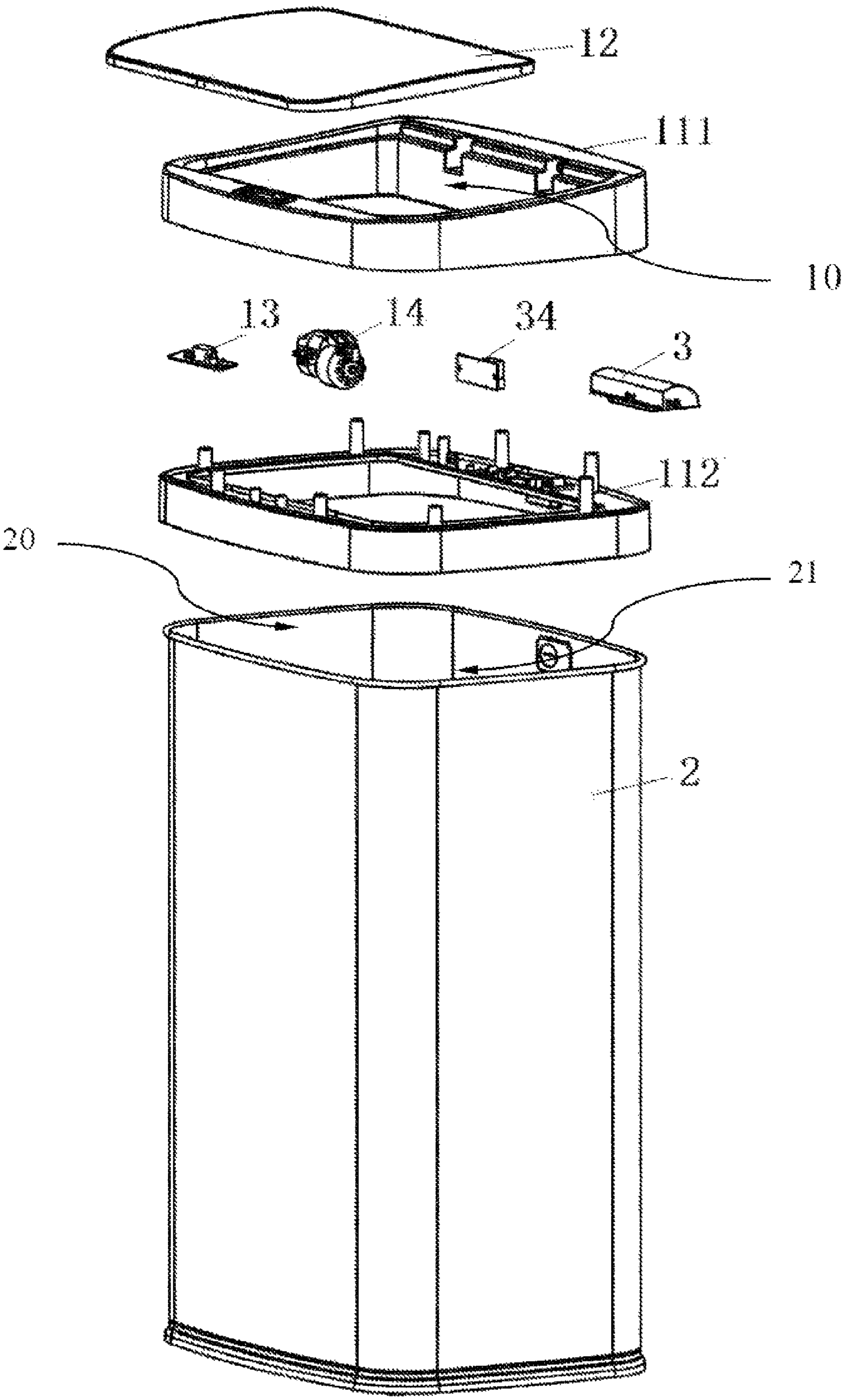
FIG. 7 an exploded structural perspective view of the sterilization and deodorization waste container as shown in FIG. 6.
Figure 8:
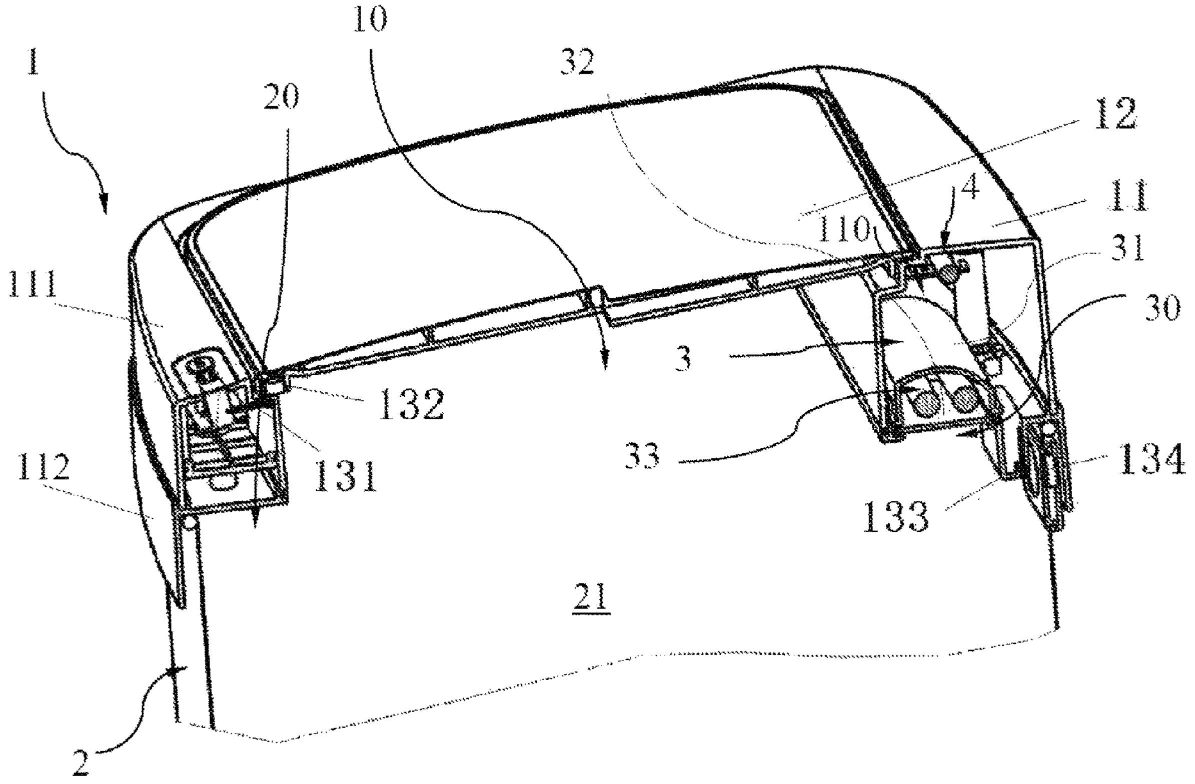
FIG. 8 is a partial structural sectional view of the sterilization and deodorization waste container with the dual-wave band ultraviolet lamp tube as shown in FIG. 6 according to the second embodiment of the invention.

Referring to FIG. 1 to FIG. 8, the invention discloses a dual-wave band ultraviolet sterilization and deodorization arrangement which is adapted to be utilized in various types of waste container, such as a waste container with its container lid pivotally connected to its container body as described in a first preferred embodiment hereinafter referencing FIG. 1-FIG. 5, and a waste container having a container lid comprising a ring shape shell configured to be mounted on the container body and a cover panel pivotally connected to the ring shape shell as described in a second preferred embodiment hereinafter referencing FIG. 6-FIG. 8. For ease of understanding, the elements of the dual-wave band ultraviolet sterilization and deodorization arrangement in both the first and second preferred embodiments are described with the same reference numbers correspondingly.

First Preferred Embodiment

This embodiment is a sterilization and deodorization waste container having dual-wave band ultraviolet lamp tube, while its container lid is not separable from its container body (such as foot-step waste container, foot-touch waste container, and etc., the present embodiment referring to the foot-touch waste container), the configurations of the foot touch control and the opening and closing operation of the container lid are conventional art that is not repeatedly described in the first embodiment. Please refer to FIG. 1 to FIG. 5.

A sterilization and deodorization waste container having a dual-wave band ultraviolet lamp tube includes a container lid 1, a container body 2 and a control circuit 13, the container body 2 being adapted for storing waste. The container lid 1 is pivotally connected at a container opening 20 above the container body 2, and the control circuit 2 and a lid opening and closing driving device 14 are installed to the container body 13. An isolation chamber 3 isolated from the air outside is arranged below the container lid 1. A light-transmitting widow is formed below the isolation chamber 3. Due to the harsh environment of the waste container, the dual-wave band ultraviolet lamp tube 33, having a II shaped configuration, is arranged in the air-isolated isolation chamber 3 and, since the ultraviolet light penetration ability is extremely weak, a transparent quartz glass 32 having very high light transmittance is embodied as the light-transmitting widow of the isolation chamber 3. The dual-wave band ultraviolet lamp tube 33 produces ultraviolet light waves, with 254 nm wavelength and 185 nm wavelength, irradiated into the waste container through a light-transmitting window 30 made of the transparent quartz glass 32, so as to use the ultraviolet light waves for sterilization and deodorization. In which, the ultraviolet light wave with 254 nm wavelength (also known as short-wave sterilization ultraviolet) has a higher photon energy, that can penetrate cell membranes and nucleus of microorganisms, destroy the molecular bonds of their DNA, and make them losing replication ability or activity and die while irradiating microorganisms. Also, the irradiating of the ultraviolet light wave with 185 nm wavelength in the air can turn O2 (oxygen) in the air into O3 (ozone). Ozone, which has a strong oxidation effect, can effectively kill bacteria. The diffusion and dispersion ability of ozone fitly make up for the shortcoming of ultraviolet that only propagates along a straight line and has dead angles and corners for disinfection, such that the function of sterilization and deodorization is strengthened.

The isolation chamber 3 is comprised of a reflector housing 31, the transparent quartz glass 32 and a sealing silicone ring 321. A peripheral edge portion of the transparent quartz glass 32 is affixed with the sealing silicone ring 321 which has a "U" shaped cross section to protect. The dual-wave band ultraviolet lamp tube 33 is arranged in the sealed isolation chamber 31 configured by the reflector housing 31 and the transparent quartz glass 32. Since ultraviolet has a strong aging ability and ozone is very corrosive, the dual-wave band ultraviolet lamp tube 33 is enclosed in the sealed isolation chamber 3, such that, on one hand, the ultraviolet light wave avoids irradiating plastic structural components of a driving control mechanism but concentrates in positions of the waste contained in the container body and, on the other hand, the ozone generated by the ultraviolet light wave irradiation does not be dispersed into an inner space of the container lid 1, causing the control circuit and the internal structural components to be corroded and oxidized by the ozone. At the same time, the dual-wave band ultraviolet lamp tube 33 is isolated and protected from being polluted. If the light-transmitting window is soiled, it merely needs to wipe the transparent quartz glass 32 to ensure sufficient ultraviolet light irradiation. The reflector housing 31 (the reflector housing 31 may be made of materials such as electroplated plastic member, a reflective filmed or a stainless steel made metal member and other materials that are not easy to age, not easy to be corroded and oxidized, the reflector housing 31 in the present embodiment referring to an electroplated plastic member) is configured to reflect ultraviolet light waves into the waste container, which greatly increases the effective light wave intensity. The ultraviolet light waves reflected through the reflector housing 31 can only be irradiated into the waste container through the transparent quartz glass 32. The transparent quartz glass 32 is capable of transmitting most of the ultraviolet light waves with 254 nm wavelength and 185 nm wavelength, that ensures most of the ultraviolets being irradiated into the waste container for sterilization and generating ozone for sterilization and deodorization in the waste container. Since silicone has strong anti-aging ability, the sealing silicone ring 321 of the present embodiment adopts a sealing silicone with a "U" shaped cross-section.

The container lid 1 is configured to be inseparable from the container body 2. A control switch is installed in the container body 2 (this control switch can be a Hall element, a position limiting switch, an angle sensor, and etc., the present embodiment utilizing a Hall element, that is, the Hall element 131). A magnet 132 is installed to the container lid 1 such that when the container lid 1 is flipped up to open, the magnet 132 leaves a detection range of the Hall element 131 with the container lid 131, the control circuit 13 receives a signal sent from the Hall element 131, and the dual-wave band ultraviolet lamp tube 33 is turned off by a ultraviolet lamp tube driver circuit 34 to cease the generation of the ultraviolets to prevent causing harm to human skin and eyes. When the container lid 1 is flipped down to close in place, the Hall element 131 detects an approaching of the magnet 132 and the control circuit 13 controls the dual-wave band ultraviolet lamp tube 33 to turn on, or otherwise, the dual-wave band ultraviolet lamp tube 33 is always remained in a turn-off state.

The parts not described in the first embodiment are the same as the conventional art.

Second Preferred Embodiment

The present embodiment is a sterilization and deodorization induction waste container having dual-wave band ultraviolet lamp tube, while its container lid is no separable from its container body (such as induction waste container, the present embodiment referring to an induction waste container), the configurations of the infrared sensing component and the opening and closing operation of the container lid are conventional art that is not repeatedly described here. Referring to FIGS. 3, 4 and 6-8, a sterilization and deodorization waste container having a dual-wave band ultraviolet lamp tube includes a container lid 1, a container body 2 and a control circuit 13, the container body 2 being used to store waste. The container lid 1 includes a ring shape shell 11 (the ring shape shell 11 is comprised of a ring shape barrel head 111 and a ring shape retainer body 122) and a cover panel 12. The cover panel 12 is pivotally connected to the ring shape shell 11. The container lid 1 is placed above a container opening 20 of the container body 2. The control circuit 13 and the lid opening and closing driving device 14 are installed in a receiving cavity of the ring shape shell 11 defined after the ring shape barrel head 111 and the ring shape retainer body 112 are affixed together. An isolation chamber 33 isolated from the air outside is arranged below the container lid 1. A dual-wave band ultraviolet lamp tube 3 is installed in the isolation chamber 33. A transparent quartz glass 33 with very high light transmittance is provided below the dual-wave band ultraviolet lamp tube 33 as a light-transmitting window. The dual-wave band ultraviolet lamp tube 33 is generate ultraviolets with a 254 nm wavelength and a 185 nm wavelength which irradiate into the waste container through the transparent quartz glass 32 of the light-transmitting window to process sterilization and deodorization through the ultraviolet light waves, wherein the ultraviolet light wave with 185 nm wavelength can produce ozone for sterilization and deodorization. In addition, due to the dispersion and diffusion ability of ozone, the ozone fills the interior space of the waste container that fitly makes up for the shortcoming of ultraviolet that only propagates along a straight line and has dead angles and corners for disinfection, such that the function of sterilization and deodorization is strengthened.

The configurations and material selections of the isolation chamber 3, the reflector housing 31, the transparent quartz glass 32, the sealing silicone ring 321, the dual-wave band ultraviolet lamp tube 33 and the sterilization and deodorization principle of the dual-wave band ultraviolet lamp tube 33 may refer to the description in the first preferred embodiment and are not repeatedly described in this embodiment.

The container lid 1 may be separated from the container body 2. The container lid 1 is comprised of a ring shape shell 11 and a cover panel 12. A control switch is installed on the container lid 1 (this control switch can be a Hall element, a position limiting switch, an angle sensor, and etc., this embodiment utilizing Hall elements, including a Hall element 131 and a Hall element 133). A magnet 134 is installed on the container body 134 such that, when the container lid 1 is separated from the container body 2, the magnet 134 leaves a detection range of the Hall element 133. After the Hall element 133 generates a signal, the control circuit 13 controls the dual-wave band ultraviolet lamp tube 33 to turn off to stop generating the ultraviolets to prevent causing harm to human skin and eyes. Similarly, the cover panel 12 is equipped with a magnet 132 such that, when the cover panel 12 is opened, the magnet 132 leaves the detection range of the Hall element 131. After the Hall element 131 generates a signal, the control circuit 13 controls the dual-wave band ultraviolet lamp tube 33 to turn off to stop generating the ultraviolets to prevent causing harm to human skin and eyes. When the cover panel 12 is closed in place and the container lid 1 is placed on the container body 2, that is only while these two conditions are met at the same time, the control circuit 13 controls the dual-band ultraviolet lamp tube 33 to turn on and operate, or otherwise, the dual-band Ultraviolet lamp tube 33 is always remained in the turn-off state. Based on the embodiments described above, the ultraviolet lamp tube 33 can also be set with a predetermined sterilization time period.

The parts not described in the second embodiment are the same as the conventional art.

In view of above first and second preferred embodiments, the isolation chamber 3 with the light-transmitting window 32 which is a transparent quartz glass sealingly mounted at an opening 30 of the reflector housing 31, the dual-wave band ultraviolet lamp tube 33, and the control circuit 13 are equipped with each other to form a dual-wave band ultraviolet sterilization and deodorization arrangement, which can be configured into an independent device for equipping with an existing waste container or built-in a waste container as illustrated in the above described first and second preferred embodiments.

In other words, according to the present invention, a dual-wave band ultraviolet sterilization and deodorization arrangement for the waste container including the container body 2 having the container opening 20 and an inner cavity 21 for storing waste and the container lid 1 configured to be mounted on top of the container opening 20 to cover the inner cavity 21 of the container body 2, wherein the dual-wave band ultraviolet sterilization and deodorization arrangement comprises the isolation chamber 3, the dual-wave band ultraviolet lamp tube 33 and the control circuit 13.

The isolation chamber 3 comprises the reflector housing 31, configured for installing below the container lid 1 of the waste container, has the light-transmitting window 32 formed in a lower side thereof. The dual-wave band ultraviolet lamp tube 33 is arranged in the reflector housing 31 and configured to generate the ultraviolets, including the direct sterilization ultraviolet light wave having a wave length between 253.7 nm to 254 nm and the ozone sterilization ultraviolet light wave having a wave length between 165 nm to 200 nm, such that the ultraviolets are arranged to propagate out through the light-transmitting window 32. Thea control circuit 13 is configured to selectively turn on the dual-wave band ultraviolet lamp tube 33 to propagate the ultraviolets and turn off the dual-wave band ultraviolet lamp tube 33 to stop propagating the ultraviolets.

Figure 1:
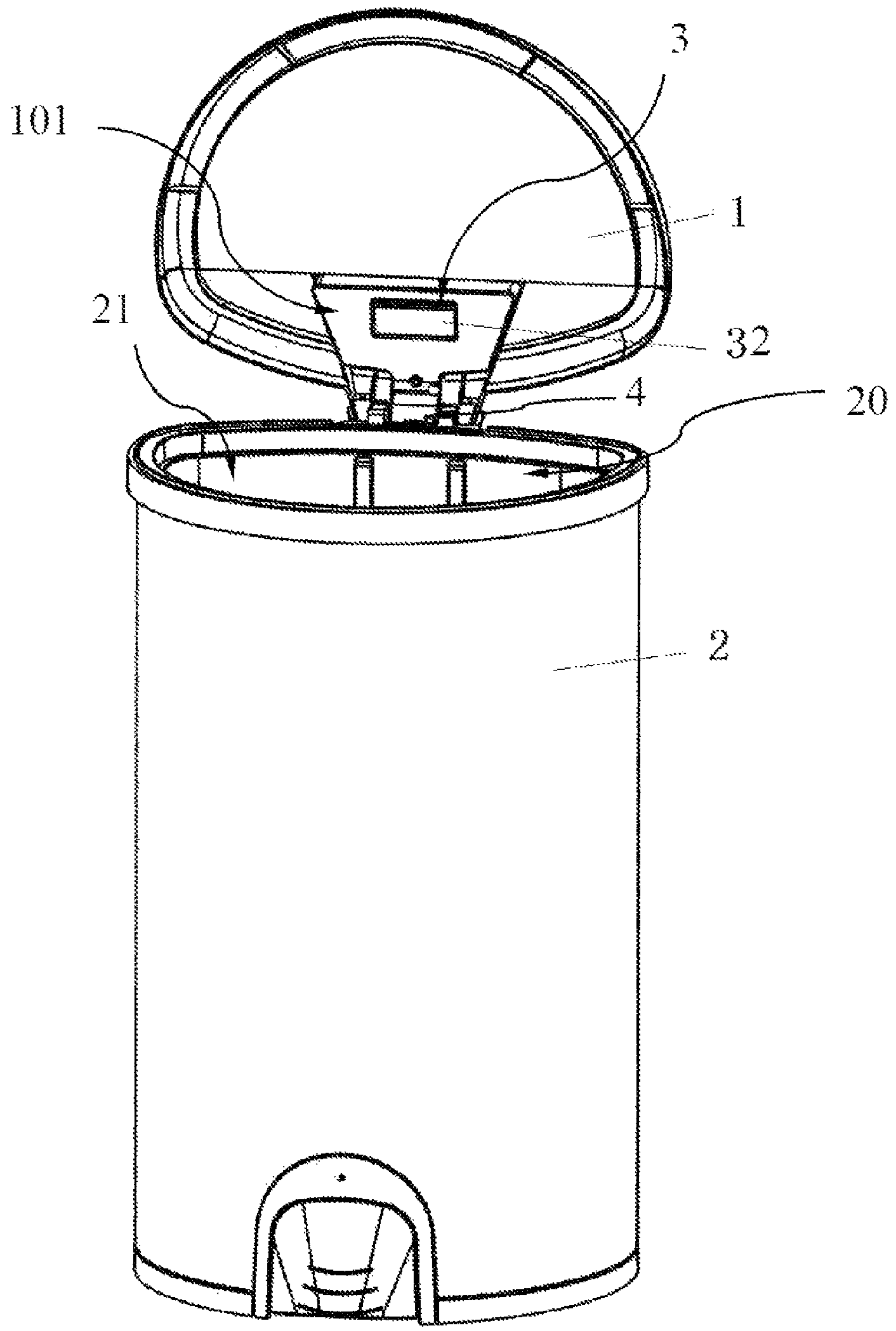
FIG. 1 is a structural perspective view of a sterilization and deodorization waste container having dual-wave band ultraviolet lamp tube according to a first embodiment of the invention.
Figure 2:
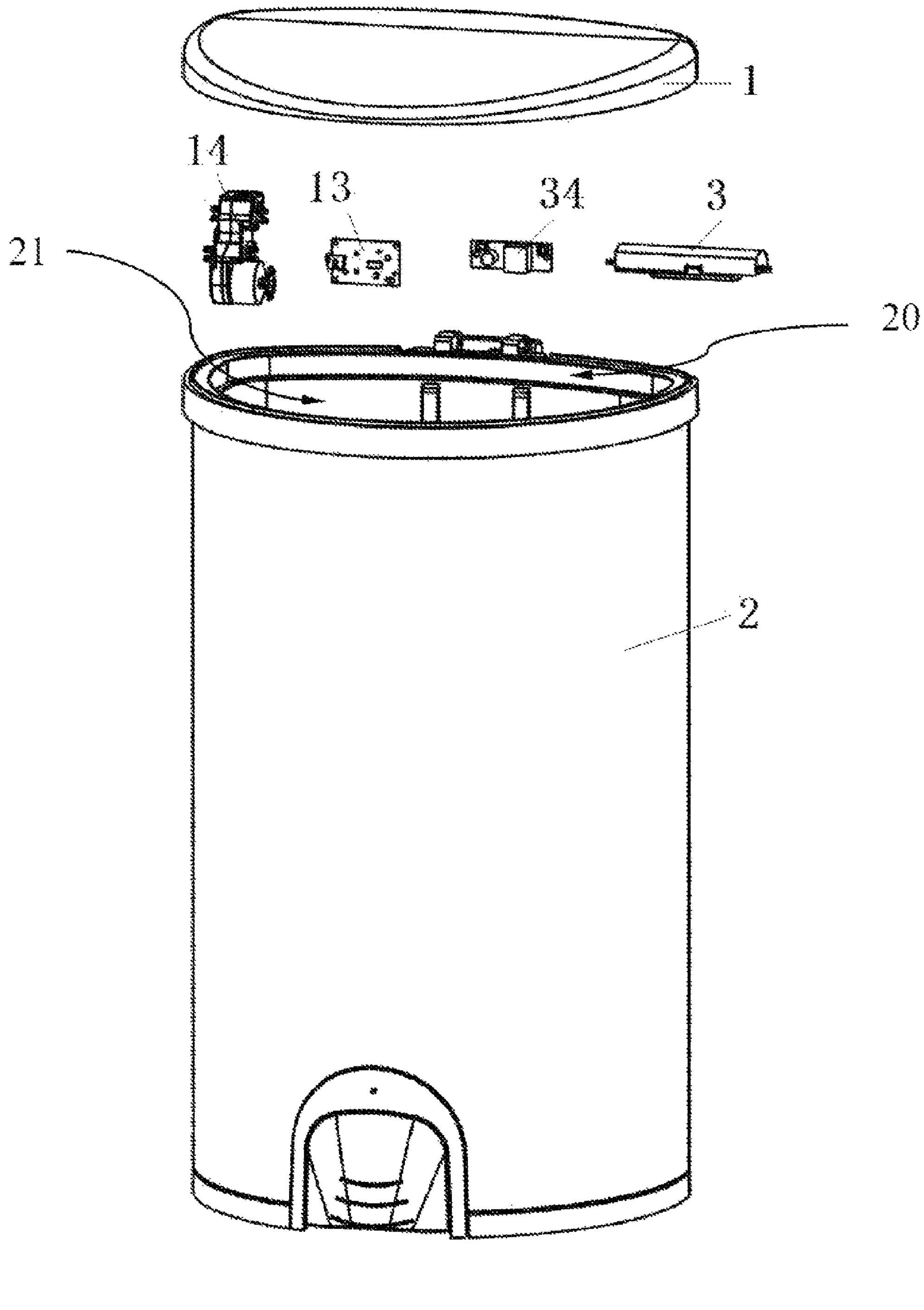
FIG. 2 is an exploded structural perspective view of the sterilization and deodorization waste container as shown in FIG. 1.
Figure 3:
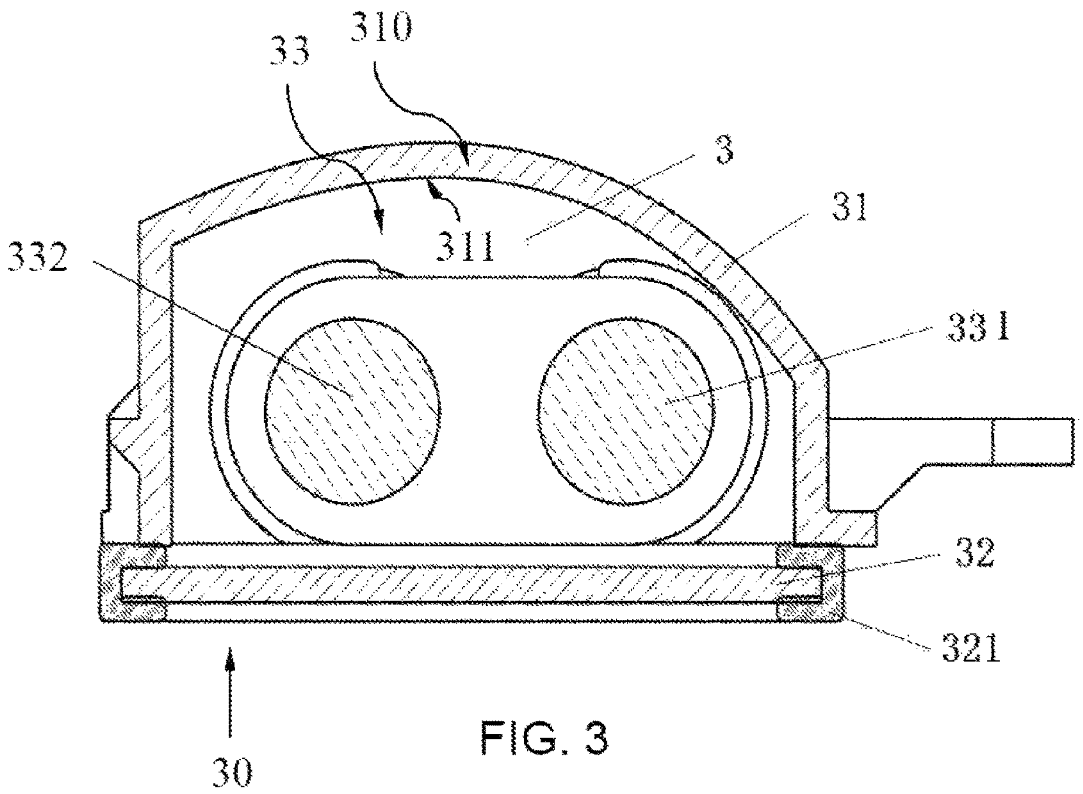
FIG. 3 is a structural sectional view of an isolation chamber of the sterilization and deodorization waste container having the dual-wave band ultraviolet lamp tube.

According to the first preferred embodiment as illustrated in FIG. 1 to FIG. 5, the container lid 1 has a side pivotally connected to a top edge of the container body 2 through a hinge mechanism 4 in such a manner that the container lid 1 is able to be flipped up about the hinge mechanism 4 to an open state as shown in FIG. 1 to open the container lid 1 with respect to the container body 2 such that the inner cavity 21 is accessible to outside, or to be flipped down about the hinge mechanism 4 to a close state as shown in FIG. 5 to close the container lid 1 with respect to the container body 2 such that the inner cavity 21 is isolated from outside by the container lid 1. A receiving shell 101 is provide to a bottom side of the container lid 1, a rear portion of the bottom side adjacent to the hinge mechanism 4 according to the first preferred embodiment, and the reflector housing 31 is fixedly mounted in the receiving shell 101 while the light-transmitting window 32 is facing the inner cavity 21 of the container body 2 when the waste container is in the close state as shown in FIG. 5.

According to the second preferred embodiment as illustrated in FIGS. 2, 4 and 6-8, the container lid 1 comprises the ring shape retainer body 11 shaped and sized to mount on a top edge of the container body 2 and defines a lid opening 10 therein. The ring shape shell 11 comprises the ring shape barrel head 111 coupled with the ring shape retainer body 112 to define a receiving cavity 110 therein. A rear side of the cover panel 12 is pivotally connected to a rear side of the ring shape shell 111 by means of a hinge mechanism 4, as shown in FIG. 8, such that the cover panel 12 is able to be flipped up about the hinge mechanism 4 to an open state to open the container lid 1 with respect to the container body 2 such that the inner cavity 21 is accessible to outside, or to be flipped down about the hinge mechanism 4 to a close state to close the container lid 1 with respect to the container body 2 such that the inner cavity 21 is isolated from outside by the cover panel 12 of the container lid 1. The reflector housing 31 is fixedly mounted in the receiving cavity 110, in a rear portion below the hinge mechanism 4 according to the second preferred embodiment, while the light-transmitting window 32 is facing the inner cavity 21 of the container body 2 no matter the cover panel 12 is in the open state with respect the ring shape shell 111 and the container body 2 or the close state with respect to the ring shape shell 111 and the container body 2 as shown in FIG. 8.

In particular, the reflector housing 31 has the opening 30 in the lower side and the light-transmitting window 32 is a transparent quartz glass fittingly and sealingly mounted at the opening 30 of the reflector housing 31 for facing the inner cavity 21 of the container body 2.

According to both the first and second preferred embodiments, referring to FIG. 3 and FIG. 4, the dual-wave band ultraviolet lamp tube 33 comprises two lamp tube bodies 331, 332 configured to propagate the direct sterilization ultraviolet light wave (253.7 nm to 254 nm wavelength) and the ozone sterilization ultraviolet light wave (165 nm to 200 nm wavelength) respectively, wherein the light-transmitting window 32 is preferred to have a size larger than the two lamp tube bodies 331, 332 so that the ultraviolets propagating from the lower sides of the two lamp tube bodies 331, 332 are transmitting through the light-transmitting window (transparent quartz glass) 32 into the inner cavity 21.

In addition, an upper side 310 of the reflector housing 31 is a curve surface coated with a reflective surface 311 arranged to face the dual-wave band ultraviolet lamp tube 33 and the light-transmitting window 32, such that a portion of the ultraviolets propagating upwards is reflected by the reflecting surface 311 to propagate downwards through the light-transmitting window 32 into the inner cavity 21 of the container body 2. Accordingly, by means of the incorporation of the light-transmitting window 32 and the reflective surface 311 of the reflector housing 31, a maximum amount of ultraviolets generated from the dual-wave band ultraviolet lamp tube 33 is capable of propagating into the inner cavity 21 of the container body 2.

According the first preferred embodiment, the control circuit 13 is configured to selectively control the dual-wave band ultraviolet lamp tube 33 to turn off to stop generating the ultraviolets while the container lid 1 is opened with respect to the container body 2 and to turn on to generate the ultraviolets while the container lid 1 is closed with respect to the container body 2. According the second preferred embodiment, the control circuit 13 is configured to selectively control the dual-wave band ultraviolet lamp tube 33 to turn off to stop generating the ultraviolets while the cover panel 12 of the container lid 1 is opened with respect to the ring shape shell 111 and the container body 2 and to turn on to generate the ultraviolets while the cover panel 12 of the container lid 1 is closed with respect to the ring shape shell 111 and the container body 2.

According to both the first and second preferred embodiments, the control circuit 13 comprises at least a detecting control element 131 and a control driving element 132 which are installed on the container body 2 and the container lid 2 respectively in such a manner that when the container lid 1 is opened, the control driving element 132 leaves a detection range of the detecting control element 131, the control circuit 13 controls the dual-wave band ultraviolet lamp tube 33 to turn off to stop generating the ultraviolets, and that when the container lid 1 is closed in place, the detecting control element 132 detects an approaching of the control driving element 131 and the control circuit 13 controls the dual-wave band ultraviolet lamp tube 33 to turn on to generate the ultraviolets.

As mentioned above, the detecting control element 131 is selected from a group consisting of Hall element, position limiting switch and an angle sensor and the control driving element 132 is embodied as a magnet.

The control driving element 132 is provided under the container lid 1 and the detecting control element 131 is provided in the waste container where the detecting control element 131 is able to detect a distance between the detecting control element 131 and the control driving element 132 to determine whether the contain lid 1 is in the close state or the open state with respect to the container body 2.

Referring to FIG. 5, according to the first preferred embodiment, the control driving element (magnet) 132 is installed at a rear edge of the container lid 1 which is overlapped with a rear top edge of the container body 2, where the detecting control element (Hall element) 131 is installed thereon, when the container lid 1 is in the close state as shown in FIG. 5. Accordingly, when the container lid 1 is flipping up to open the container body 2, the control driving element 132 is moving away from the detecting control element 131, and a signal is sent from the detecting control element 131 to trigger the ultraviolet lamp tube driver circuit 34, which is powered by an external power source or internal power source such as one or more batteries (not shown in Figures), to turn off the dual-wave band ultraviolet lamp tube 33 to cease the generation of the ultraviolets to prevent causing harm to human skin eyes while the inner cavity is accessible to outside. The dual-wave band ultraviolet lamp tube 33 is always remained in a turn-off state.

Also, when the container lid 1 is flipping down until the container lid 1 is closed in place with respect to the container body 2 as shown in FIG. 5, the control driving element 132 is moving towards the detecting control element 131 until it is overlapped on the detecting control element 131, i.e. the container lid 1 is fully closed in place to isolate the inner cavity 21 of the container body 2 from outside, the detecting control element 131 detects the approaching of the control driving element 132 and sends out another signal to trigger the ultraviolet lamp tube driver circuit 34 to turn on the dual-band ultraviolet lamp tube 33 to generate ultraviolets to propagate into the inner cavity 21 of the container body 2.

It is worth mentioning that the installation locations of the pair of detecting control element 131 and the control driving element 132 can be exchanged.

Referring to FIG. 8, according to the second preferred embodiment, the cover panel 12 of the container lid 1 is configured to open or close the lid opening 10 and the container opening 20 simultaneously. The control circuit 13 comprises two pairs of detecting control element 131, 133 and control driving element 132, 134, wherein the two detecting control elements 131, 133 are installed on the ring shape shell 11 and the two control driving elements 132, 134 are installed on the container body 2 and the cover panel 12 respectively, such that when one of the detecting control elements 131, 133 leaves the corresponding control driving element 132, 134 while either the cover panel 12 or the ring shape shell 11 is opened with respect to the container body 2, the control circuit 13 controls the dual-wave band ultraviolet lamp tube 33 to turn off to stop generating the ultraviolets, and that when both the ring shape shell 11 and the cover panel 12 are closed in place with respect to the container body 2, the detecting control elements 131, 133 detect an approaching of the corresponding control driving element 132, 134 and the control circuit 13 controls the dual-wave band ultraviolet lamp tube 33 to turn on to generate the ultraviolets.

In particular, referring to FIG. 8, the first pair of the detecting control element 131 and the control driving element 132 are installed to a front edge of the ring shape shell 11 and a front edge of the cover panel 12 respectively so as to control the turn-on and turn-off operation of the dual-wave band ultraviolet lamp tube 33 with respect to the closing and opening of the cover panel 12 with respect to the container body 2. The second pair of the detecting control element 133 and the control driving element 134 are installed to a rear portion of the ring shape shell 11 (a rear edge of the ring shape retainer body 112 of the ring shape shell 11) and a rear top edge of the container body 2 respectively.

Accordingly, referring to FIG. 8, when the container lid 1 is separated from the container body 2, such as detaching the ring shape shell 11 upwards from the container body 2, the control driving element 134 leaves a detection range of the detecting control element 133 and the detecting control element 133 sends a signal to trigger the ultraviolet lamp tube driver circuit 34 of the control circuit 13 to turn off the dual-wave band ultraviolet lamp tube 33 to stop generating the ultraviolets to prevent causing harm to human skin and eyes. Also, when the cover panel 12 is operated to flip up to open the container body 2, i.e. the inner cavity 21 of the container body 2 is accessible to outside through the lid opening 10 and the container opening 20, the control driving element (e.g. magnet) 132 leaves the detection range of the detecting control element 131 (e.g. Hall element) and the detecting control element 131 generates a sign to trigger the ultraviolet lamp tube driver circuit 34 of the control circuit 13 to turn off the dual-wave band ultraviolet lamp tube 33 to stop generating the ultraviolets to prevent causing harm to human skin and eyes.

When container lid 1 is placed on the container body 2, i.e. the ring shape shell 11 is normally mounted on the container body 2, and the cover panel 12 is flipping down until the cover panel 12 is closed in place with respect to the ring shape shell 11 and the container body 2 as shown in FIG. 8, the control driving element 132 is moving towards the detecting control element 131 until it is overlapped on the detecting control element 132, i.e. the cover panel 12 is fully closed in place to isolate the inner cavity 21 of the container body 2 from outside, the detecting control element 131 detects the approaching of the control driving element 132 and sends out a signal to trigger the ultraviolet lamp tube driver circuit 34 to turn on the dual-band ultraviolet lamp tube 33 to generate ultraviolets to propagate into the inner cavity 21 of the container body 2. In other words, only while these two conditions are met at the same time, that is both the cover panel 12 and the ring shape shell 11 are closed in place, the control circuit 13 controls the dual-wave band ultraviolet lamp tube 33 to turn on and operate, or otherwise, the dual-wave band ultraviolet lamp tube 33 is preferred to be remained in the turn-off state.

In accordance with another aspect of the invention, a sterilization and deodorization method for the waste container is provided, the method comprises:

(a) turning on the dual-wave band ultraviolet lamp tube 33, sealed in the isolation chamber 3 provided below the container lid 1 of the waste container 2, to generate ultraviolets, including the direct sterilization ultraviolet light wave having a wavelength between 240 nm to 280 nm and the ozone sterilization ultraviolet light wave having a wavelength between 165 nm to 200 nm, propagating through the light-transmitting window 32 of the isolation chamber 3 into the inner cavity 31 of the waste container, while the container lid 1 is in a close state with respect to the container body 2; and (b) turning off the dual-wave band ultraviolet lamp tube 33 to stop generating the ultraviolets while the inner cavity 21 of the container body 2 is accessible to outside.

In which, in the step (b), the inner cavity 21 of the container body is accessible to outside when the container lid 1 is opened with respect to the container body 2 and/or the ring shape shell is separated from the container body.

The above description is merely preferred embodiments of the invention and is not intent to limit the invention, and any modification, equivalent substitution, improvement, and etc. made within the spirit and principles of the invention should be included within the scope of the claimed invention. One skilled in the art will understand that the embodiment of the present invention as shown in the drawings and described above is exemplary only and not intended to be limiting.

What is claimed is:

1. A dual-wave band ultraviolet sterilization and deodorization arrangement for a waste container including a container body having a container opening and an inner cavity for storing waste and a container lid configured to be mounted on top of the container opening to cover the inner cavity of the container body, wherein the container lid comprises a ring shape shell arranged to be mounted on top of the container body, and a cover panel pivotally connected to the ring shape shell for closing a lid opening of the ring shape shell and the container opening of the container body, wherein the dual-wave band ultraviolet sterilization and deodorization arrangement comprises:

an isolation chamber comprising a reflector housing, configured for installing below the container lid of the waste container, having a light-transmitting window formed in a lower side thereof;

a dual-wave band ultraviolet lamp tube arranged in the reflector housing and configured to generate ultraviolets, including a direct sterilization ultraviolet light wave having a wave length between 253.7 nm to 254 nm and an ozone sterilization ultraviolet light wave having a wave length between 165 nm to 200 nm, such that the ultraviolets are arranged to propagate out through the light-transmitting window; and a control circuit configured to selectively turn on the dual-wave band ultraviolet lamp tube to propagate the ultraviolets and turn off the dual-wave band ultraviolet lamp tube to stop propagating the ultraviolets, wherein the control circuit comprises two pairs of detecting control element and control driving element, wherein the two detecting control elements are installed on the ring shape shell and the two control driving elements are installed on the container body and the cover panel respectively, such that when one of the detecting control elements leaves the corresponding control driving element while either the cover panel or the ring shape shell is opened with respect to the container body, the control circuit controls the dual-wave band ultraviolet lamp tube to turn off to stop generating the ultraviolets, and that when both the ring shape shell and the cover panel are closed in place with respect to the container body, the detecting control elements detect an approaching of the corresponding control driving element and the control circuit controls the dual-wave band ultraviolet lamp tube to turn on to generate the ultraviolets.

2. The dual-wave band ultraviolet sterilization and deodorization arrangement, as recited in claim 1, wherein the reflector housing has an opening in the lower side and the light-transmitting window is a transparent quartz glass fittingly and sealingly mounted at the opening of the reflector housing for facing the inner cavity of the container body.

3. The dual-wave band ultraviolet sterilization and deodorization arrangement, as recited in claim 2, wherein a reflective surface is provided at an upper side of the reflector housing, wherein a lower side of the dual-wave band ultraviolet lamp tube sealingly arranged in the isolation chamber faces the light-transmitting window of the isolation chamber and an upper side of the dual side of the dual-wave band ultraviolet lamp tube faces the reflective surface of the isolation chamber such that a portion of the ultraviolets propagating upward is reflected by the reflecting surface to propagate downwards through the light-transmitting window into the inner cavity of the container body.

4. The dual-wave band ultraviolet sterilization and deodorization arrangement, as recited in claim 1, wherein the control circuit is configured to selectively control the dual-wave band ultraviolet lamp tube to turn off to stop generating the ultraviolets while the container lid is opened with respect to the container body and to turn on to generate the ultraviolets while the container lid is closed with respect to the container body.

5. The dual-wave band ultraviolet sterilization and deodorization arrangement, as recited in claim 3, wherein the control circuit is configured to selectively control the dual-wave band ultraviolet lamp tube to turn off to stop generating the ultraviolets while the container lid is opened with respect to the container body and to turn on to generate the ultraviolets while the container lid is closed with respect to the container body.

* * * * *